United States Patent

Bourke

Patent Number: 5,163,840
Date of Patent: Nov. 17, 1992

[54] METHOD AND APPARATUS FOR DENTAL TREATMENT

[76] Inventor: Kevin J. Bourke, 1 High Street, East Maitland, NSW, Australia, 2320

[21] Appl. No.: 720,178

[22] Filed: Jun. 24, 1991

[30] Foreign Application Priority Data

Jun. 25, 1990 [AU] Australia ............................. PK0795

[51] Int. Cl.$^5$ .............................................. A61C 3/00
[52] U.S. Cl. .......................................... 433/6; 433/7; 433/24
[58] Field of Search ................... 433/6, 7, 24, 229, 18; 128/861, 62 A

[56] References Cited

U.S. PATENT DOCUMENTS

| | | | |
|---|---|---|---|
| 2,257,709 | 9/1941 | Anderson | 128/861 |
| 4,591,341 | 5/1986 | Andrews | 433/6 |
| 4,919,612 | 4/1990 | Bergersen | 433/6 |

Primary Examiner—Cary E. O'Connor
Attorney, Agent, or Firm—Darby & Darby

[57] ABSTRACT

A method and apparatus are disclosed for dental treatment of jaw and tooth malformations. The apparatus is made of a soft, resilient material and includes upper and lower compartments which are shaped so as to conform to a patient's teeth. The upper compartment opens upwardly and the lower compartment opens downwardly, so that they can receive the patient's upper and lower teeth, respectively. Each compartment includes a plurality of flexible protrusion members which extend from its side walls so as to contact the teeth when the device is worn. Particular protrusions in the vicinity of selected teeth are enlarged or removed so as to achieve movement of those teeth in order to improve the alignment of the patient's teeth and jaw. The method involves placing the device in a patient's mouth so as to receive the patient's teeth and retaining the device within the patient's mouth for a predetermined period of time, during which the patient is at rest.

9 Claims, 2 Drawing Sheets

METHOD AND APPARATUS FOR DENTAL TREATMENT

FIELD OF THE INVENTION

This invention is directed to the field of human and animal health and, in particular, concerns medico/dental methods of treatment whereby unsatisfactory physical conditions can be ameliorated and well-being promoted. The invention also includes within its ambit an improved device for use in carrying out such methods.

BACKGROUND OF THE INVENTION

The invention is predicated upon my research-based discovery that certain known physical complaints, maladies and other physical conditions can be treated in a manner not previously contemplated. These complaints/physical conditions are briefly discussed immediately below. The invention whereby they are treated is set forth thereafter.

A significant number of people, some researchers put the figure as high as 25%, suffer from a complaint variously called Myofascial Pain Dysfunction Syndrome, or Temporo Mandibular Joint (TMJ) disease. While the exact cause of this complaint (for convenience, hereafter simply called TMJ), is not fully known, and is in fact much in dispute, the consensus is that psychological stress factors associated with living in the 20th Century are at least partially to blame. Researchers generally agree that many painful conditions of the head and neck joint systems can be attributed to derangement of the TMJ.

Previous methods of treating TMJ have generally involved the use of splint therapy (using plastics as a material base). While a certain measure of success has been achieved, the results, overall, have been less than satisfactory.

Tooth crowding, as it is simply called in the dental profession, is a prime example of a less than satisfactory physical condition. Almost all cases of tooth crowding are caused by insufficient space in the bones of the jaw to accommodate the teeth. Procedures and devices to correct this condition, involving treatment of the jaw bone by orthopaedic appliances, are of course known. Again however, the condition remains a considerable cause of concern.

My invention is directed towards a method of treatment whereby the foregoing complaints/conditions are overcome, or at least substantially alleviated.

In one aspect, the invention provides a method of treatment whereby a device is positioned in the mouth of a patient which, when so positioned, serves to maintain the upper and lower teeth of the patient in a spaced apart, substantially, pressure-free, class 1 relationship. The device is then retained within the mouth of the patient for a predetermined period of time, for at least a portion of which the patient is at rest. The condition of rest may be established by positive external steps, or naturally. Other method aspects of the invention will appear hereafter.

The expression "the patient is at rest" is meant to indicate that, at a time of rest, the patient is wearing the device passively, i.e., without exerting thereon any positive chewing or other pressure. A patient at rest is best illustrated by a person asleep. However, the expression is not necessarily so confined. In like fashion, the aforementioned "predetermined period of time" is frequently, but not necessarily, equatable to a period in which the wearer is asleep.

In a further aspect, the invention provides a device for carrying out the method as above defined. The device is adapted to be comfortably positioned within the mouth of a patient to be treated by the method of the invention. The device, which is typically of a pharmaceutically acceptable non-irritant material and is usually of one piece construction, is provided with means which fit between the upper and lower teeth and function to keep them separated. As an uncomfortably fitting device would be deleterious to the performance of the method of the invention (which requires the upper and lower teeth to be maintained in a naturally spaced apart class 1 relationship), the separation of the upper and lower teeth is achieved without force on either the upper or lower jaw.

The device of the invention is made of a flexible, resilient material such as rubber. It includes upper and lower compartments shaped and sized to receive the upper and lower sets of teeth. Each compartment includes a plurality of prongs or fingers which project into the compartment from its bounding walls so as to resiliently engage the wearer's teeth. Gradual adjustment of the orientation of the teeth can be achieved by shortening or removing prongs on the walls of the compartments towards which the teeth are to move.

BRIEF DESCRIPTION OF THE DRAWINGS

The foregoing brief description, as well as various objects, features and advantages of the present invention will be understood more completely from the following detailed description of presently preferred, but none the less illustrative, embodiments, of the invention with reference being had to the accompanying drawings in which.

DETAILED DESCRIPTION OF THE PREFERRED EMBODIMENT

As mentioned above, a device 10 in accordance with the present invention is adapted to be comfortably and safely positioned within the mouth of a user in the general manner of a sporting person's mouthpiece or mouth guard. It is suitably of unitary one-piece construction, made of soft flexible rubber of the type employed in the manufacture of nipples for baby bottles. Alternatively, it can be made from a suitable inert plastic or silicon(e)-based material.

Figure 1:
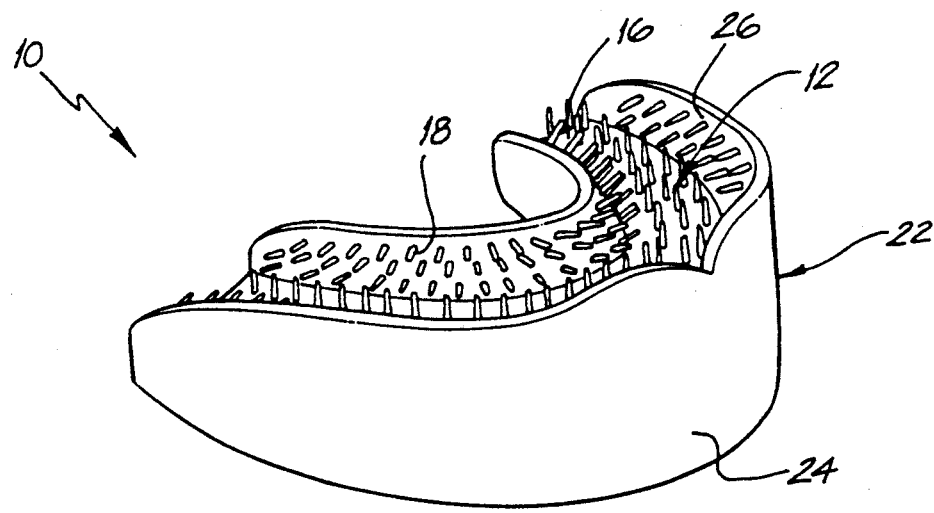
FIG. 1 is a perspective view of a dental appliance or device incorporating objects and features of the present invention.
Figure 2:
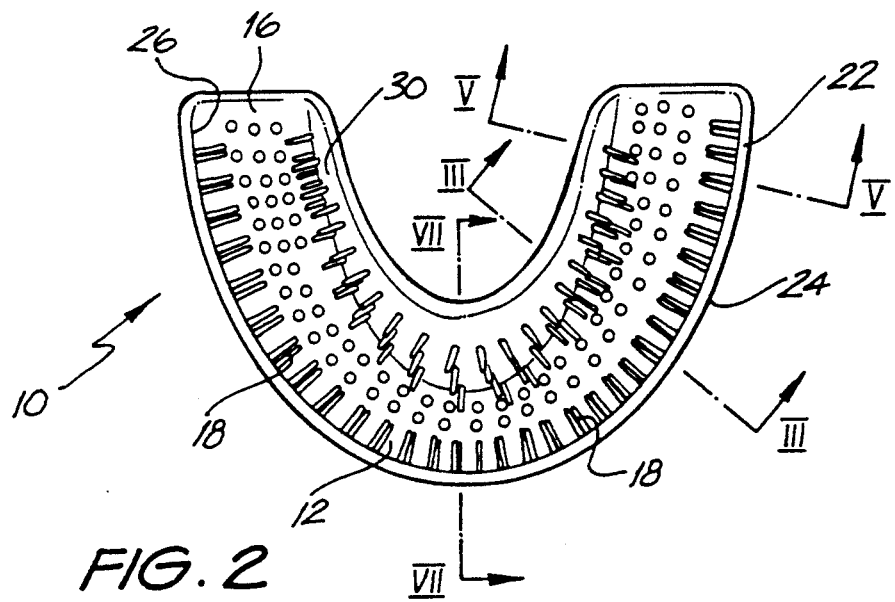
FIG. 2 is a top view of the device of FIG. 1.
Figure 3:
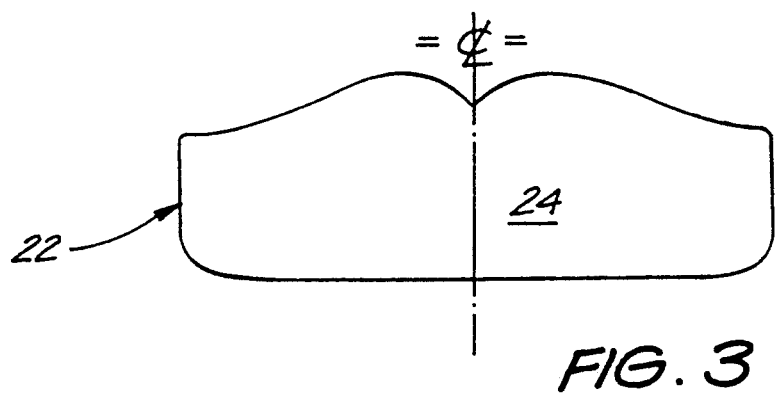
FIG. 3 is a front view of the device of FIG. 1.
Figure 4:
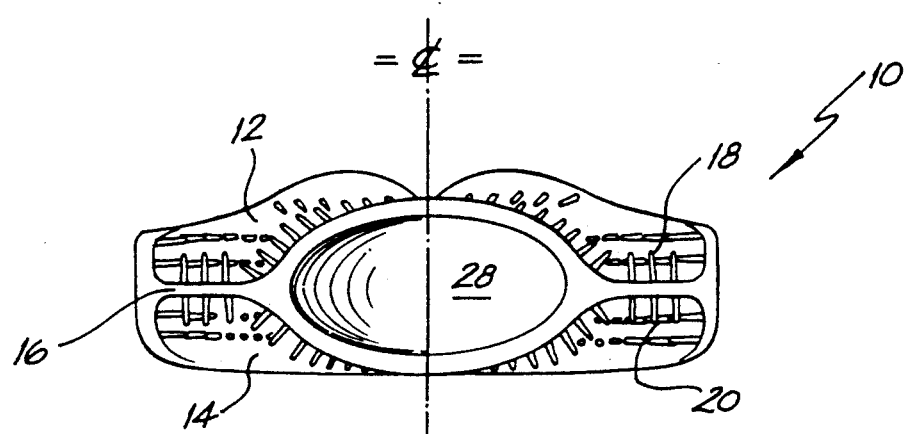
FIG. 4 is a rear view of the device of FIG. 1.
Figure 5:
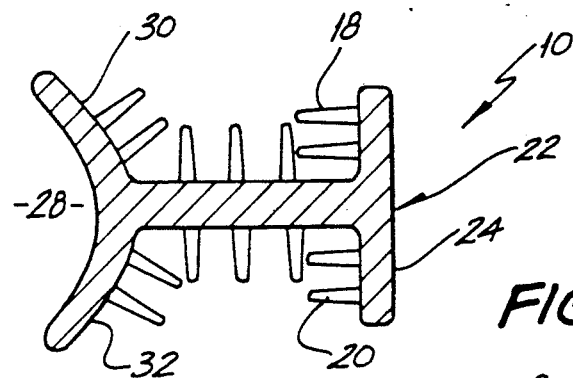
FIG. 5 is a sectional view taken along the line V—V in FIG. 2 and looking in the direction of the arrows.
Figure 6:
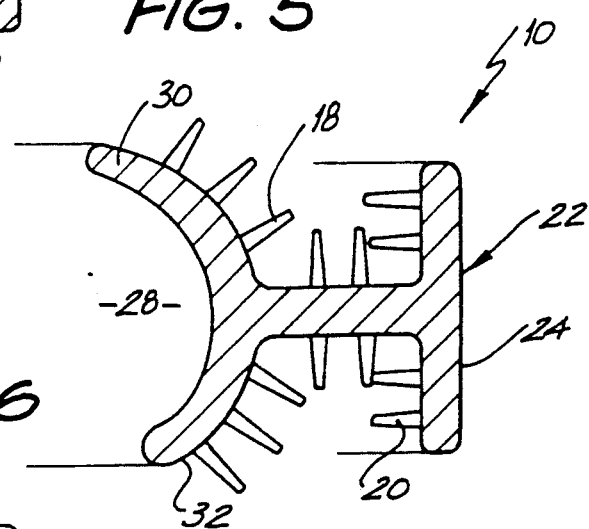
FIG. 6 is a sectional view taken along the line VI—VI in FIG. 2 and looking in the direction of the arrows.
Figure 7:
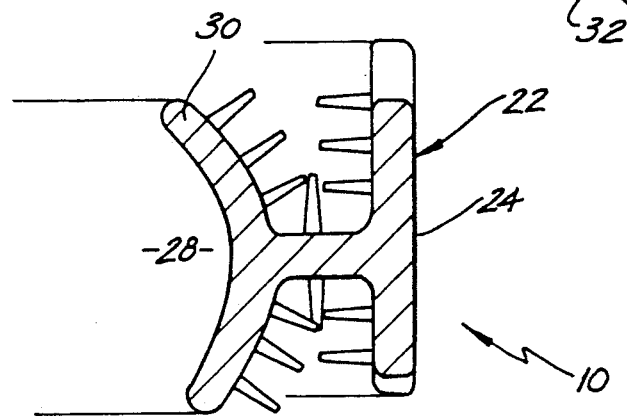
FIG. 7 is a sectional view taken along the line VII—VII in FIG. 2 and looking at the direction of the arrows.

Examined in further detail, the device 10, viewed from directly above, has an overall configuration which approximates the arcuate configuration of a person's (upper and lower) teeth (see FIG. 2). There is an upper, inwardly disposed, generally U-shaped compartment 12, of the same arcuate extent as the overall device, which, in use, will accommodate the downwardly extending upper teeth of the wearer, and a lower similarly configured but reversely disposed compartment 14, of the same arcuate extent, to receive the upwardly extending lower teeth of the wearer. The compartments 12, 14 are spaced and separated by a central, generally horizontally disposed, member 16 which is common to both compartments (its opposite surfaces respectively constituting the base of the upper compartment, and the top of the lower compartment). Each compartment is provided throughout with a series of projecting protuberances 18, 20, preferably 1-2 mm in diameter, which do not prevent, or are arranged to permit, entrance of the teeth and which will be in contact with the teeth when the device is in place for use. One of the functions of the protuberances, which will be discussed further below, is to promote isotonic exercise (better blood flow) of the relevant musculature.

At its front, the device has an arcuately configured vertically disposed continuous member 22, the front surface 24 (i.e., the surface seen by the viewer when the device is in the slightly open mouth of the wearer) of which is smooth and planar and the rear surface 26 of which constitutes respective vertical surfaces of the teeth accommodating compartments. At its rear, the device is cut away to provide an inwardly extending smooth-walled cavity 28, which, in use, will accommodate the tongue of the subject. The reverse surface of the cavity is inwardly inclined and constitutes the opposite respective surfaces 30, 32 of the teeth accommodating compartments 12 and 14, respectively.

As just described, the upper and lower compartments 12, 14 are in the same vertical plane. However, this planar relationship may be varied. For example, the lower portion of the device may be constructed so as to be more anteriorly situated.

The protuberances will generally be equi-spaced and dimensioned, normally disposed to the surface from which they protrude and are arranged in parallel rows. However, this regime can be varied as required. One such instance is in the case where the method and device of the invention are employed in the course of the treatment of a patient in respect of whom diagnosis has indicated the need to move the Condylar head of the mandible forward in the Glenoid fossa. The consequence of such movement is the creation of a space between the posterior teeth, which in turn can lead to an unhealthy condition in the teeth supporting tissues. To assist in such a situation, the device is constructed so that some of the protuberances, in particular the protuberances towards the ends of the upper and lower compartments (i.e., the rearwardly situated protuberances when the device is in position), are of increased width and height, a typical such increase being of the order of 50-150% (e.g., 2-3 mm, and up to 5 mm respectively). This will provide the contact that is necessary to maintain the health of the posterior teeth and supporting tissues during treatment.

This last-mentioned embodiment of the device, wherein appropriately located selective protuberances are differently dimensioned than the others, represents a significant ancillary feature of my invention.

To meet individual requirements (which, naturally, will vary enormously between large framed mature adults at one end of the scale, and small children at the other), the device is of course constructable in a number of sizes. It will at the same time be appreciated that the aforementioned characteristic features are common to all sizes. It is usually desirable for the upper and lower parts of the device to be in a "Dental Class 1 relationship", with a thickness of 2-3 mm of material on the biting surface. This, however, is subject to variation as required.

When the device is positioned within the mouth of the patient, the upper and lower teeth will be accommodated in the respective compartments with the protuberances in contact therewith. With the device thus positioned, the wearer may go to sleep. When the device is in the mouth of a person asleep, the device is being passively worn by a person at rest.

As to the predetermined period of wearing, this will of course be widely variable. However, in the case of a person who wears the device during his (her) normal night's sleep, which is itself subjectively determined by each person's individual requirements, a typically predetermined period of time would be within the range 6 to 10 hours.

My research indicates that treatment in accordance with the method of the invention constitutes a substantive step forward in the art. While not intending to be bound by any particular theory of operation, the following is presented by way of non-limiting hypothesis.

When the device is being worn passively by a subject at rest, the effect of the treatment is to de-stress the muscles of the stomato-gnathic system and, indeed, all the muscles of the head and neck. This appears to be achieved by a reprogramming of the head and neck musculature, whereby the motor unit activity (nerves) in the muscles is lowered and the blood supply to said muscles is increased.

It is generally accepted that a substantial percentage of all the motor and sensory nerve fibers that leave and enter the brain are associated with the lower region of the face. The teeth in fact have a proprioceptor component that transfers information to the cerebral cortex of the brain. When the device to be used in the method of the invention is in place (i.e., fitted in the mouth of the subject to be treated), it functions to transmit information to the brain, the "message" of which is that the teeth can be clenched or ground without damage to the muscles of the overall craniofacial system. The end consequence is better blood flow through the head and neck muscles, better oxygenation of the muscles and elimination of a variety of symptoms, the most common of which are painful trigger points in the head and neck (i.e., headaches and the like). This consequence is reflected in a more restful night's sleep for the wearer.

When the device is fitted in the mouth of the patient, the Condylar head of the mandible is moved downward and forward away from the superior-posterior part of the Glenoid fossa. With the Condylar head so positioned, TMJ pain can be alleviated.

Forward and downward movement of the mandible has the effect of verticalizing the teeth (and alveolar processes), and thus creating a Class 1 type of occlusion. This is accepted as being a desirable type of occlusion.

Where the device is fitted to the mouth of a patient, and worn passively (e.g. with the subject asleep) for a period of 8 to 10 hours, the effect of the method of the invention is to expand the teeth and jaws. The elastodontic action achieved by this (usually nocturnal) use, whereby the dental arches are expanded, is of particular value where applied to the treatment of a child whose teeth are "crowded". Positive use during a subject's waking period (with chewing and the like), for short periods such as 20 minutes at a time, will of course be usefully supplementary.

In elaboration of the immediately foregoing, the device is of course "sized" to complement the arch form of the patient (for arch expansion, the lingual section of the device is desirably about 3 mm larger in width than the arch of the patient). With the device inserted, space must exist on the buccal or outside section of the device to allow the teeth to move buccally.

Clinical studies indicate that it is possible to alter the individual positions of each tooth, in a buccolingual or linguo-facial position, simply by selectively removing projections on either the outside or the inside of the trough, whether upper or lower.

EXAMPLE 1

Suppose that a child of 7 years had some crowding of the teeth in the lower arch, whereby the lower right central and lateral incisors were bodily displaced towards the lingual as a result of insufficient space in the arch. This malocclusion could be rectified by wearing the device nocturnally, and also preferably actively (chewing) for some short periods of active use during waking hours. For expansion purposes (orthopaedic) laterally the device needs to be marginally (about 3 mm) wider laterally than the arch form, and because of the inherent nature of the material, the teeth and alveolar bone will tend to conform to the shape of the device. This manner of movement may be considered orthopaedic movement.

Additionally, other movement (orthodontic) may be achieved by removing the latex Projections on the facial or labial surfaces of the device in the region of the lower malaligned central and lateral incisors. The effect of all this would be to move the malpositioned teeth into correct alignment by pushing the central and lateral incisor labially by means of pressure from the lingual projections.

Alveolar bone (the bone which contains the tooth roots) can be altered in form by pressure arising from the lips, cheek, tongue and even the finger, as is done by children who have the habit of sucking their finger. That is, the environment of the teeth and alveolar bone can in large measure overwhelm the genetic tendency.

Thus, when the natural matrix of the teeth and alveolar bone, i.e., the lips, teeth and tongue, are nullified by wearing the device nocturnally, then the matrix for the teeth and jaws is now altered, and the arch form is now markedly influenced by the shape of the arch form of the device.

EXAMPLE 2

Suppose that due to thumb sucking, the upper anterior teeth are positioned too far labially and a loss of coupling with the lower anterior teeth has taken place, due in part also to a lack of competence in the lips and the habit of mouth breathing. If this condition exists in a child in early years (2 to 6), then nocturnal use of the device will not only train the child to breathe through the nose, but will alter the shape of the anterior arch form to comply to the shape of the arch form of the present device, i.e., the shape which exists between the projections on the vertical walls of the appliance.

Further to that, the individual positions of the teeth can be adjusted to move the deciduous teeth lingually by removing the projections lingual to that particular tooth. In such a case, the only pressure on that particular tooth would now be coming from the biting or horizontal surface of the appliance, and from the projections coming from the labial surface, tending to move the tooth to the lingual. If the projections on the horizontal surface were also to be removed then the only force on the tooth would be directed towards the lingual. Thus, malaligned teeth in the upper anterior arch could be repositioned to conform to a better arch form.

Similarly in the posterior segment of the mouth, if the upper buccal teeth were in a cross bite relationship to the lower teeth, then to correct this malocclusion in a young child in particular, the vertical projections and horizontal projections contacting the upper teeth (in cross bite) would be removed, allowing the lingual projections to exert an outward force on the teeth all night, thus moving them into a proper relationship to the lower teeth over a period of several months. In such a case as the above, it would also be advisable for the child to actively munch on the appliance, for about 20 minutes daily.

If a tooth or several teeth are to be moved through bone in the dental arch, then other teeth and tissue must act as anchorage, this principle is well recognized in Orthopaedics and orthodontics. Thus one or two teeth are moved, while the rest of the arch remains stable.

The uniqueness of the present system of expansion can be appreciated by considering the present state of the art. Until now, if it became necessary to move teeth through alveolar bone, then either of the following methods had to be employed:

1. The use of the commonly seen arch wires with brackets on the teeth;
2. Orthopaedic dental appliances, made of a hard material, where an impression was required of the patient's mouth, where the teeth or bone or both were moved with wires or screws;
3. In more recent times, with elastodontic appliances, an impression had to be taken of the patient's mouth and a cast made on which the appropriate appliance would be made.

EXAMPLE 3

In accordance with the present method of Orthopaedic-Orthodontic treatment, it is not necessary to take an impression and make a casting, all that is necessary for orthopaedic movement is to select an appliance with the desired arch form for that particular patient, and have the patient use the appliance while sleeping. This situation is particularly applicable to young children, where bone growth in the maxilla and mandible and tooth movement through that bone is more readily accomplished. The tooth movement being accomplished by the appropriate adjustment to the soft projections, with an instrument such as a fingernail clipper.

Clinical tests show that, if a young patient is in a skeletal Class 2 relationship where the mandible is retruded in relation to the maxilla, wearing the device overnight will, on many occasions, correct that relationship to a skeletal class 1 position. Previously this could only be accomplished by using a much harder material like plastic or acrylic as in a bionator.

The above movement (translation) of the mandible is also applicable to all ages, but the results are more rapid in the youngest patients.

When the device is used nocturnally by an Adult, tooth grinding is eliminated, and so pathological stresses are greatly nullified in the Temporo mandibular joint, giving rise to more complete relaxation to not only the muscles of the craniofacial system, but to all the muscles of the body, even down to the feet.

Where specific details are set forth in the foregoing description, such as size, particular configurations and the like, such details are to be regarded as no more than illustratively of a preferred form of the invention. As long as the basic criteria are observed, all such noncritical matters can be varied in accordance with situational requirements. Likewise, while specific functions and modes of action have been set forth, others are within the purview of the overall invention.

Although preferred forms of the invention have been described for illustrative purposes, those skilled in the art will appreciate that many additions, modifications, and substitutions are possible without departing from the scope and spirit and of the invention as defined in the accompanying claims.

What is claimed is:

1. A method for treating jaw and tooth malformations, said method being directed at moving one or more of the patient's teeth and making use of an apparatus made of a soft, resilient material and having upper and lower compartments which are generally U-shaped so as to conform upwardly and the lower compartment opening downwardly so as to receive a patient's teeth, each compartment having side walls and a connecting wall joining the side walls and a plurality of flexible protrusion members extending from the walls into the interior of the compartments so as to contact the patient's teeth when the device is worn, said method comprising the steps of selecting a device in which the protrusion members in the vicinity of the teeth to be moved and on a surface of the teeth which is to be moved away from said protrusion members are one of longer and thicker than the protrusion members contacting the other surfaces of said teeth, placing the device in the mouth of a patient so that the upper and lower teeth are received in the upper and lower compartments of the device respectively, and retaining the device within the patient's mouth for a predetermined period of time, during a substantial portion of which the patient is at rest.

2. The method of claim 1 utilized to enlarge the dental arch of a patient, said method comprising the step of selecting a device which is shaped so that its arch is marginally larger than the dental arch of the patient.

3. The method of claim 2 wherein the arch of the device is about 3 mm larger than the patient's arch.

4. A method for treating jaw and tooth malformations, said method making use of an apparatus made of a soft, resilient material and having upper and lower compartments which are generally U-shaped so as to conform generally to a patient's teeth, the upper compartment opening upwardly and the lower compartment opening downwardly so as to receive a patient's teeth, each compartment having side walls and a connecting wall joining the side walls and a plurality of flexible protrusion members extending from the walls into the interior of the compartments so as to contact the patient's teeth when the device is worn, members being substantially equal in length and thickness, said method being directed at moving at least one tooth, said method comprising the steps of foreshortening the protrusion members in contact with the surface of said at least one tooth which is to be moved towards an opposed wall of said device, placing the device in the mouth of a patient so that the upper and lower teeth are received in the upper and lower compartments of the device respectively, and retaining the device within the patient's mouth for a predetermined period of time, during a substantial portion of which the patient is at rest.

5. The method of claim 4 utilized to enlarge the dental arch of a patient, said method comprising the step of selecting a device which is shaped so that its arch is marginally larger than the dental arch of the patient.

6. The method of claim 5 wherein the arch of the device is about 3 mm larger than the patient's arch.

7. An apparatus for treating jaw and tooth malformations, a main body made of a soft, resilient material and having upper and, lower compartments which are generally U-shaped so as to conform generally to a patient's teeth, the upper compartment opening upwardly and the lower compartment opening downwardly so as to receive a patient's teeth, each compartment having side walls and a connecting wall joining the side walls and a plurality of flexible protrusion members extending from the walls into the interior of the compartments so as to contact the patient's teeth when the device is worn, certain of said protrusion members positioned to contact a first surface of selected teeth being foreshortened in comparison with those positioned to contact another surface of said teeth, to achieving gradual movement of said teeth towards said foreshortened protrusion members when said apparatus is worn by a patient.

8. An apparatus in accordance with claim 7 wherein all protrusion members are substantially the same size, the protrusion members positioned to contact said first surface having been selectively cut short so as not to contact the same.

9. An apparatus for treating jaw and tooth malformations, a main body made of a soft, resilient material and having upper and lower compartments which are generally U-shaped so as to conform generally to a patient's teeth, the upper compartment opening upwardly and the lower compartment opening downwardly so as to receive a patient's teeth, each compartment having side walls and a connecting wall joining the side walls and a plurality of flexible protrusion members extending from the walls into the interior of the compartments so as to contact the patient's teeth when the device is worn, certain of said protrusion members positioned to contact a first surface of selected teeth being one of longer than and thicker than those positioned to contact another surface of said teeth, to achieving gradual movement of said teeth away from said certain protrusion members when said apparatus is worn by a patient.

* * * * *